United States Patent [19]
Heggeness et al.

[11] Patent Number: 5,558,674
[45] Date of Patent: Sep. 24, 1996

[54] DEVICES AND METHODS FOR POSTERIOR SPINAL FIXATION

[75] Inventors: Michael H. Heggeness, Houston, Tex.; Brian J. Doherty, Atherton, Calif.

[73] Assignee: Smith & Nephew Richards, Inc., Memphis, Tenn.

[21] Appl. No.: 169,998

[22] Filed: Dec. 17, 1993

[51] Int. Cl.$^6$ .................................................. A61B 17/70
[52] U.S. Cl. ......................................... 606/61; 606/73
[58] Field of Search ............................... 606/61, 73, 69; 411/410, 405, 403, 402

[56] References Cited

U.S. PATENT DOCUMENTS

| | | | |
|---|---|---|---|
| 375,206 | 12/1887 | Shelton | 411/403 |
| 3,741,205 | 6/1973 | Markolf et al. | 606/73 X |
| 4,493,317 | 1/1985 | Klaue | 606/73 X |
| 5,171,279 | 12/1992 | Mathews | 606/61 X |
| 5,176,678 | 1/1993 | Tsou | 606/61 |
| 5,176,679 | 1/1993 | Lin | 606/61 |

FOREIGN PATENT DOCUMENTS

| | | | |
|---|---|---|---|
| 442377 | 2/1936 | United Kingdom | 411/403 |

OTHER PUBLICATIONS

White, A. A. and Panjabi, M. M., *Clinical Biomechanics of of the Spine*, 2nd Ed., Ch. 8, pp. 528–568, 579–615 (1990).

Montesano, P. X., et al., "Biomechanics of Cervical Spine Internal Fixation", Spine, 16:S10–16 (1991).

Krag, M. H., "Biomechanics of Thoracolumbar Spinal Fixation: A Review", Spine 16:S84–97 (1991).

Grob, D., et al., "Posterior Occipitocervical Fusion: A Preliminary Report of a New Technique", Spine 16:S17–23 (1991).

Nazarian, S. M. and Louis, R. P., "Posterior Internal Fixation with Screw Plates in Traumatic Lesions of the Cervical Spine", *Spine* 16:S64–71 (1991).

Jeanneret, B., et al., "Posterior Stabilization of the Cervical Spine with Hook Plates", Spine 16:S56–63 (1991).

Anderson, P. A., et al., "Posterior Cervical Arthrodesis with AO Reconstruction Plates and Bone Graft", Spine 16:S72–79 (1991).

Sasso, R. C., et al., "Posterior Fixation of Thoracic and Lumbar Spine Fractures Using D C Plates and Pedicle Screws", *Spine* 16:S134–139 (1991).

Daniaux, H., et al., "Application of Posterior Plating and Modifications in Thoracolumbar Spine Injuries – Indication, Techniques, and Results", Spine 16:S125–133 (1991).

Smith, S. A., et al., "Cervical Spine Locking Plate: In Vitro Biomechanical Testing", *Eur. Spine J.*, 1:222–225 (1993).

Aebi, M., et al., "Treatment of Cervical Spine Injuries with Anterior Plating – Indications, Techniques, and Results", *Spine* 16:S38–44 (1991).

Ripa, D. R., et al., "Series of Ninety-Two Traumatic Cervical Spine Injuries Stabilized with Anterior ASIF Plate Fusion Technique", Spine 16:S46–55 (1991).

Haas, N., et al., "Anterior Plating in Thoracolumbar Spine Injuries", Spine 16:S100–110 (1991).

Bayley, J. C., et al., "The Syracuse I–Plate", *Spine* 16:S120–124 (1991).

(List continued on next page.)

*Primary Examiner*—Tamara L. Graysay
*Attorney, Agent, or Firm*—Pravel, Hewitt, Kimball & Krieger

[57] ABSTRACT

Disclosed are novel devices and methods for modular occipital/spinal fixation, general bone fixation, as well as skull fracture repair, wherein a novel orthopedic plate designed for unicortical engagement of the bone, particularly the occiput, is employed which exhibits greater stability and safety over conventional methods. Also disclosed is a novel method and device for posterior spinal fixation, preferably involving the use of a locking screw/plate assembly for posterior facet screw fixation of cervical and thoracic vertebrae. A novel locking screw and locking tool is further disclosed which may be used with the inventive orthopedic plate and spinal fixation devices as well as other orthopedic devices.

22 Claims, 7 Drawing Sheets

OTHER PUBLICATIONS

Thalgott, J., et al., "Reconstruction of Failed Lumbar Surgery with Narrow AO DCP Plates for Spinal Arthrodesis", *Spine* 16:S170–175 (1991).
Danek Product Bulletin – TSRH Spinal System (1992).
Synthes Product Bulletin – "Modular Spine System".
AcroMed Product Advertisement (1993).
Official Gazette (Sept. 7, 1993, p. 276) – U.S. Pat. No. 5,242,446 to Steffee, A. D. ("Connector for a Spinal Column Corrective Device").
Smith & Nephew Richards, Inc. Product Bulletin – Biomechanical Analysis:Rogozinski Spinal Rod System.

DEVICES AND METHODS FOR POSTERIOR SPINAL FIXATION

BACKGROUND OF INVENTION:

1. Field of Invention

The present invention is related to novel devices and methods for spinal fixation, including in one aspect posterior spinal fixation, particularly posterior cervical fixation, utilizing a plate and locking screw system, designed for improved stability and safety over devices presently in use. The invention is also directed to novel devices and methods for occipital/spinal fixation, particularly fixation of the occiput to the posterior side of the cervical vertebrae, utilizing both the inventive device and method of posterior spinal fixation as well as other spinal fixation systems. The invention is also related to the use of orthopedic plates for stabilization of fractured bones, including skull bone following a surgical craniotomy or accidental fracture. Finally, the present invention is related to a novel locking screw system for use in orthopedic plate/screw fixation devices.

2. Description of Related Art

Occipital/cervical fixation:

Occipital/cervical fixation, although not a commonly performed procedure, is indicated for instability of the craniocervical junction resulting from trauma, degenerative disease, inflammatory arthritis, or malignancy.

Several techniques have been tried in recent years to improve the ease and reliability of occipital/cervical fixation, many of which are described by White and Panjabi in *Clinical Biomechanics of the Spine*, 2nd Ed. (1990). One common technique for posterior occipital/cervical fixation involves the use of wires. In particular, the occiput is fused to the upper cervical spine by a set of bilateral wires which are threaded through holes drilled into the C1 and C2 vertebrae and up through holes drilled into the occiput. Alternatively, occipital/cervical fixation may be accomplished by the use of Luque rods with intracranial and sublaminar wiring. While stability is good, these techniques are dangerous in that there is a serious risk of cerebrospinal fluid leak and/or bleeding from the sagittal sinus due to the placement of the holes in the occiput.

Another method of posterior occipital/cervical fixation is the use of a single plate molded according to the anatomy of the head and the cervical spine. At one end, the plate is screwed into the occiput, and at its other end the plate is screwed or wired to the vertebrae. One such plate is a Y-plate, as discussed by Grob, D. et al., "Posterior Occipitocervical Fusion," 16 *Spine* S17–S24, (1991). Here, the "arms" of the plate are attached to the C1 and C2 vertebrae by transarticular screws while the proximal end of the plate is attached to the occiput by screws. The C1–C2 fusion is accomplished by use of a technique developed by Magerl wherein two non-locking screws connect the two vertebrae, at an upward 30° angle, through the top of the C2 lamina, across the C1–C2 articulation, and into the lateral mass of C1.

Alternatively, bilateral fixation plates can be used for subaxial (i.e. vertebrae below C1) fusion, comprising the use of two reconstruction plates. According to Grob and associates [(16 *Spine* S17 (1991)], the plates are fixed to the occiput by screws through the skull, and then they are fixed distally to the lateral masses of the subaxial vertebrae. To attach the plates to the vertebrae, the drilling of the holes is directed cranially and parallel to the joint surface and 20°–30° laterally to avoid damage to the vertebral artery and nerve root.

The use of internal fixation to the occiput is made challenging by the extreme variability in the thickness of the skull itself and the rather major penalties which can complicate these procedures. The current procedures generally known in the industry for occipital/spinal fixation involve insertion of screws and/or intracranial wires through the very thin bone of the cerebellar fossa. Resulting complications of occipital fixation thus include the creation of dural leaks, direct trauma to the brain, penetration of the large intracranial venous sinuses, and iatrogenic meningitis. Other complications associated with any internal fixation device, such as hardware loosening, hardware pull out, and hardware fracture, for example, can also occur.

Consequently, it is desirable to have a method of occipital/spinal fixation wherein the occipital fixation device is placed in an optimal location on the skull, ideally the thickest bone, for increased safety as well as optimal stability. Such a method is best accomplished by a modular system whereby the surgeon is able to mount a plate to a desired location on the occiput, and then attach a separate spinal fixation device, such as rod or plate, for example, posteriorly to the desired vertebrae. The superior end of the spinal fixation device can then be adapted to attach to the plate, or a third device can be used to connect the plate to the spinal fixation device.

Posterior Spinal Fixation:

The use of segmental screw fixation has revolutionized the practice of thoracic and lumbar spinal surgery. Implants with screws which lock rigidly to the plate are extremely stable and allow the surgeon considerable freedom in performing very aggressive destabilizing surgery. This is often to the patient's advantage in cases of extreme spinal instability, fracture, or tumor. Examples of such implants include the Kaneda device (vended by AcroMed, for example.) for anterior thoracic and lumbar use, for example, and the Cotrel-Dubousset (manufactured by Sofamor) and Texas Scottish Rite (vended by Danek) pedicle screw configuration methods for the posterior thoracic and lumbar spine.

A current method of posterior cervical fixation involves C1–C2 sublaminar posterior wiring used in combination with Luque rods. While this method works fairly well to immobilize the spine, there is an increased risk of spinal cord injury due to the necessity of passing multiple sublaminar wires through the cervical spinal canal. Other posterior spinal fixation methods include spinous process wires and facet wires typically used in the lower cervical spine, Halifax clamps which clamp together the lamina of the C1 and C2 vertebrae, and hook plates placed underneath the lamina of the lower vertebrae involved and fixed to the articular process of the upper vertebrae by a screw (as described by Jeanneret, B. et al., "Posterior Stabilization of the Cervical spine with Hook Plates," 16 *Spine* S56–S63 (1991)).

Another method of posterior spinal fixation involves the use of screws and/or plates. Anderson and associates in their article "Posterior Cervical Arthrodesis with AO Reconstruction Plates and Bone Graft" (16 *Spine* S72–S79 (1991)) discuss fixation of the cervical spine by the use of these non-locking, lateral mass plates which are attached to the vertebrae by screws inserted into the vertebrae at a 30°–40° cranial (i.e. upward) direction. Each screw attaches one vertebra, such that the vertebrae are connected to each other only by means of the plate. The plates are malleable and have different hole spacings to accommodate variations in patient size and anatomic levels to be fused.

A similar technique for posterior cervical fixation using lateral mass screws and plates was originally described by Roy-Camille, et al. (*Recent Advances in Orthopaedics,* B. McKibbin, Ed., p.51–87 (Churchill-Livingston, Edinburgh 1979) and is explained in greater detail by Nazarian and Louis (16 *Spine* S64–71 (1991)). This technique also involves placing a screw into each individual lateral mass and then attaching or connecting the vertebrae together by means of a non-locking plate. The direction of screw placement is different from the Magerl method, discussed below; however, the purpose of both methods is to obtain bicortical purchase through the lateral mass of a single vertebra without penetration of the facet joint.

All of the foregoing methods are examples of segmental fixation; however, they do not rigidly attach the screws to the plate. All of these implants, for example, may have problems when used on a grossly unstable spine, such as that created by a complete cervical vertebrectomy. The non-locking lateral mass plates, such as the reconstruction plate vended, for example, by AO, also require an extraordinary degree of technical expertise by the surgeon. Acquiring bicortical purchase with these lateral mass screws requires that the screw be placed "freehandedly" to within millimeters of the vertebral artery and the exiting cervical nerve root. Injury to either of these structures may have devastating consequences for the patient.

The Magerl method, as discussed, for example, by Montesano, et al. ["Biomechanics of Cervical Spine Internal Fixation" (16 *Spine* S10–S16 (1991)], involves the attachment of the anatomically unique C1 and C2 vertebrae by two non-locking screws. The screws are engaged at an upward angle by insertion from the tip of the lamina of C2, across the C1–C2 articulation, and into the lateral mass of C1. The screw length is about 18–20 mm, and the angle of purchase is 30° in an upward (i.e. cranial) direction. This method of fixation, however, is a relatively dangerous procedure in that there is a great risk of damage to the exiting cervical nerve root and the vertebral artery, similar to the risks associated with the use of non-locking lateral mass plates discussed above.

Another means of obtaining posterior internal fixation of the spine is the use of screws to transfix the facet joints. This method, as applied to the lumbar spine, has been described by M. Heggeness and S. Esses, 16 *Spine* S266–S269 (1990). This method has also been applied in the anatomically unique (and complex) C1–C2 level of the spine, as described by Montesano, et al., 16 *Spine* S10–S16 (1991).

In light of the problems associated with existing devices and methods for posterior spinal fixation, in particular posterior cervical fixation, it is desirable to have a device and method that affords adequate immobilization of the spine, including a grossly unstable spine, without posing a significant threat to the vertebral artery or cervical nerve root.

Plate/locking screw systems for spinal fixation:

Presently, there are very few locking screw devices on the market for use in spinal fixation. Perhaps the most commonly used locking screw is that used in the cervical locking plate manufactured by AO/Synthes ("CSLP"). This screw consists of a cylindrical screw head, drilled coaxially with the long axis of the screw shaft. That is, there is a smaller set screw in the head. The walls of the head are also slotted, so placement of the set screw expands the walls of the head, locking it into the plate. Aspects of this screw include minimal risk of screw pull-out. This method, however, has the disadvantage that it is easy to accidentally misplace or drop the smaller set screw into the surgical wound during use.

Another locking screw system is the "ORION" plate (sold by Danek), which is also a "two-screw" system. In this system, one larger screw is placed into the hole of the locking plate and then positioned into the bone like other screw/plate devices. However, a second screw with a much larger head is inserted into a smaller hole adjacent to the first hole containing the larger screw. Once the larger screw is in the proper position in the bone, the smaller screw is inserted into the plate as described above and torqued down until a portion of the head of the smaller screw covers a portion of the head of the larger screw, thus preventing the larger screw from backing out. This method also requires the use of an additional small "locking screw" which may be dropped or misplaced. The use of this type of locking screw also adds bulk to the implant and may impinge the visceral structures of the patient.

The AMS Company manufactures another type of locking screw/plate system utilizing a single screw. The screw comprises two sets of threads on the longitudinal piercing portion of the screw. The set of threads immediately subjacent to the screw head are designed to engage into a threaded hole contained within the locking plate. The lower set of threads function to engage the bone. Thus in this system, when the screw is torqued to engage the lower set of threads into the bones, the screw is simultaneously "locked" into the plate via threadable engagement of the upper threads of the screw with the hole in the locking plate. While this system is advantageous in that only one screw is required, the disadvantage of this system is that the screw placement function and the locking function are combined, thereby making it difficult for the surgeon to "feel" where he or she may be in the bone being penetrated. The quality of bone/screw purchase is thus more difficult for the surgeon to assess.

It is therefore desirable to have a locking plate/screw system requiring only one locking screw, but where the locking function and the bone placement function are separate for safer and easier bone purchase. It is also desirable to minimize the number of components in the locking mechanism.

SUMMARY OF THE INVENTION

The present invention, in certain embodiments, is directed to a novel modular method for posterior occipital/spinal fixation, comprising (a) attaching at least one plate to an optimal position on an occiput, wherein the plate comprises a posterior surface and an anterior surface, (b) attaching at least one longitudinal spinal stabilizing device to the posterior surface of at least two spinal vertebrae, including an inferior-most vertebra, and wherein the longitudinal spinal stabilizing device has a superior end and an inferior end, and (c) connecting the superior end of the longitudinal spinal stabilizing device to the plate. The modular design of the present invention allows for independent placement of the plate or plates and the spinal stabilizing device or devices for optimal safety and stability. In particular, it is easier to mount the plate to a more desired location on the occiput, usually the thickest bone of the occiput.

The present invention also relates to a novel fixation device for use in posterior occipital/spinal fixation, wherein the fixation device comprises a plate having a posterior surface and an anterior surface, a connecting means for connecting the plate to the occiput, and a mounting means for mounting the plate to a longitudinal spinal stabilizing device that is fixedly attached to the posterior surfaces at least two vertebrae. In the preferred embodiment of the present invention, the plate has at least two angled bores positioned bilaterally to one another, and the connecting means is preferably a screw engaged in each of the bores for unicortical, angled engagement of the plate to the occiput. The mounting means of the plate is preferably an elevated platform which is adapted for attachment to a longitudinal spinal stabilizing device, such as cervical or thoracic rods, plates, or wires, for example. In particular, the platform preferably contains at least one bore for engagement of the longitudinal spinal stabilizing device by a second connecting means such as a screw or wires, for example.

Advantages of certain embodiments of the present inventive method of occipital/spinal fixation over other existing methods include:

(1) a modular design which allows for independent placement of the plate and the spinal stabilizing device for optimal safety and stability. This is particularly important since the safe insertion of the cervical spine lateral mass screws, for example, effectively dictates the position and orientation of other occipital/cervical plates beyond any substantial control of the surgeon. While a bendable occipital/cervical plate improves somewhat the ability of the surgeon to position the plate on the occiput, the present invention, with its modular design, gives the surgeon much greater flexibility;

(2) improved stability of the occipital fixation device to the occiput by positioning the screws in a converging or diverging direction to minimize or prevent screw pull-out; and (3) engagement of only one cortex of the occiput (i.e. the posterior cortex) while maintaining good stability, thus improving safety by greatly decreasing the risk of penetrating the brain or intracranial venous sinuses, or causing cerebrospinal fluid leak.

The present invention, in certain embodiments, is also directed to a novel posterior spinal stabilizing device and method which may also be adapted for use with the present inventive occipital/spinal fixation method. Specifically, the inventive posterior spinal stabilizing device comprises (a) a longitudinal spinal stabilizing member further comprising a superior end, an inferior end, an anterior surface, a posterior surface, at least one downwardly-angled bore contained therethrough, and at least one upwardly-angled bore contained therethrough, wherein said at least one upwardly-angled bore is located on the inferior end of said member; (b) a first screw engaged within each of one or more said downwardly-angled bore for engagement of two vertebrae; and (c) a second screw engaged within each of one or more said upwardly-angled bore for engagement of an inferior-most vertebra. In particular, the present inventive method of posterior spinal stabilization allows for tri-cortical and bi-cortical purchase of the bony structures of the vertebrae, particularly the cervical vertebrae, without significant threat to the vertebral artery or cervical nerve root. Moreover, the angle of screw placement, as defined by the inventive posterior spinal stabilizing member, is the optimal angle for screw engagement of the cortices necessary to achieve these results.

The present invention is also related to a novel method for stabilizing a skull bone fracture or a skull fragment resulting from a craniotomy, for example. In both cases, stabilization of the skull bone is achieved by aligning the inventive plate (or a minor variation thereof) over the line of fracture or junction and then inserting a screw through the angled bores and into the posterior cortex of the skull for unicortical engagement. The present invention is a safer and better method of skull repair as compared to other methods in which either a metal plate, for example, is used to cover the opening in the skull resulting from the craniotomy, or the previously removed skull fragment is replaced without the aid of any stabilizing device to stabilize and prevent the fragment from subsiding into the brain.

The inventive plate can also be used as a general bone fixation device similar to the inventive method of posterior spinal stabilization. For example, the inventive plate may be first attached to a portion of the skull, and then one end of a separate longitudinal stabilizing device, such as a rod or plate, may be mounted to the inventive plate. The other end of the longitudinal stabilizing device is then mounted to another bone of the skull, such as the mandible. Similarly, the inventive plate can be mounted to other bone surfaces in the body to stabilize the bone or a fracture.

Finally, the present invention is directed to a novel locking screw which can be used in conjunction with any orthopedic device that typically requires a locking screw. In particular, the present inventive locking screw system comprises the use of a single screw comprising a head and a longitudinal cylindrical piercing member integral with the head, wherein the head further comprises (a) an exterior surface defining the circumference of the head, (b) at least one depression specifically a locking means, positioned on the exterior surface of the screw head for locking said head, preferably via crimping engagement, within the orthopedic device, and (c) a top portion integral with the exterior surface of the screw head, wherein the top portion has a socket for insertion of a tool for engaging the screw through or into said orthopedic device.

The inventive locking screw is advantageous in that only a single screw is required, in addition to the plate, to achieve locking as opposed to other systems wherein an additional piece, such as another screw, is required to lock the screw into the plate and bone. Further, when the inventive screw is used to also penetrate the bone, the function of inserting the screw into the bone and the function of locking the screw into the plate are separate, thereby enabling the surgeon to better feel the location of the screw in the bone for safer and more effective screw placement.

BRIEF DESCRIPTION OF THE FIGURES

The objects, advantages, and features of the invention will become more apparent by reference to the drawings which are appended hereto, wherein like numerals indicate like parts and wherein an illustrated embodiment of the invention is shown, in which.

DETAILED DESCRIPTION OF THE PREFERRED EMBODIMENTS

Posterior spinal fixation

The present invention, in certain embodiments, is related to a novel device and method for posterior spinal fixation using a novel plate and locking screw design. In particular, the present method is directed to novel facet screw fixation of at least two vertebrae, preferably utilizing a longitudinal spinal stabilizing device and a locking screw. In the preferred embodiment of the present invention, the device is attached to at least two adjacent vertebrae in the C-2 through C-7 cervical spinal region. However, the inventive device may also be used for stabilization of at least two adjacent vertebrae in the upper thoracic region of the spine.

Figures 5, 6, 7:
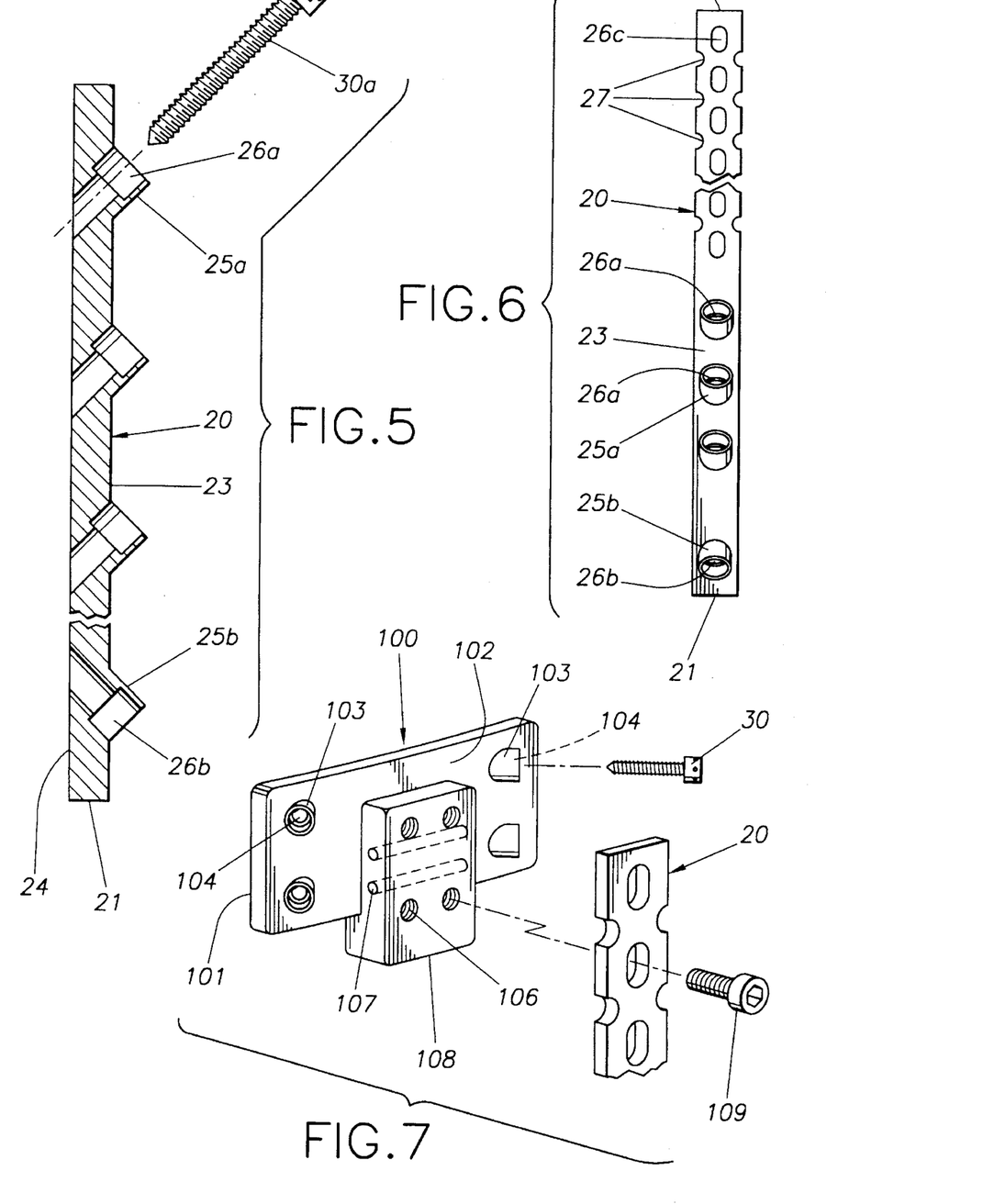
FIG. 5 is a cross-sectional side view of the present inventive posterior longitudinal spinal stabilizing device showing the downwardly- and upwardly-angled bores.
FIG. 6 is a posterior or front view of the present inventive longitudinal spinal stabilizing device.
FIG. 7 is a perspective view of the present inventive plate.

The present invention comprises attaching a longitudinal spinal stabilizing member, with at least two fasteners, preferably screws, to the posterior cortices of the lateral masses of at least two vertebrae. Referring to FIGS. 5 and 6, the longitudinal spinal stabilizing member (20) comprises a superior end (22), an inferior end (21), an anterior surface (24), and a posterior surface (23). The inventive longitudinal stabilizing member further includes at least one, more preferably at least two, downwardly-angled bore (26a) and at least one upwardly-angled bore (26b). Preferably, a lip (25a and 25b) extends outward from each bore and functions, in part, to maintain the angle of the bore, and consequently the angle of the screw, as well as aid in the locking mechanism of a locking screw.

Figures 3, 4:
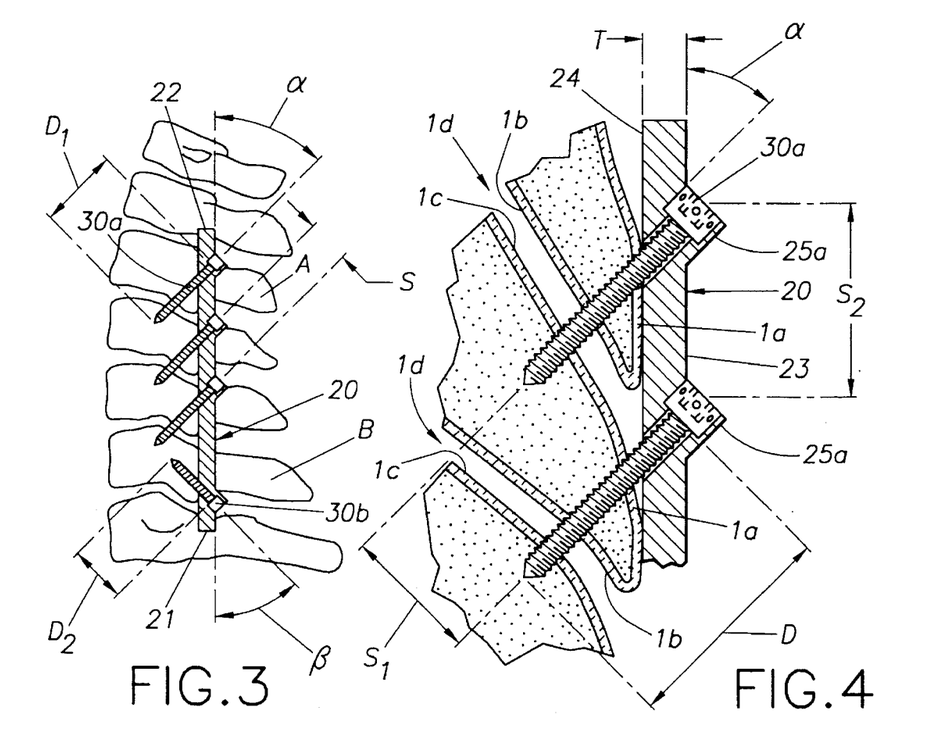
FIG. 3 is an enlarged cross-sectional side view of the cervical spinal region showing attachment of the inventive posterior longitudinal spinal stabilizing device to four cervical vertebrae using three downwardly-angled screws penetrating the posterior cortices of lateral masses of the vertebrae and one upwardly-angle screw penetrating the posterior cortex of the inferior-most vertebra.
FIG. 4 is an enlarged view of FIG. 3, showing tri-cortical purchase of the vertebrae with the present inventive posterior longitudinal spinal stabilizing device and the inventive locking screw.

As shown in FIGS. 3–5, a first screw (30a) is inserted through a downwardly-angled bore (26a), and a second screw (30b) is inserted through the upwardly-angled bore (26b). The first screw is then inserted through the posterior cortex of the lateral mass of a first vertebra (1a), through the inferior articular surface of the first vertebra (1b), and finally through the superior articular surface of the second vertebra (1c) subjacent to the first vertebra. The space between the inferior articular surface of the first vertebra and the superior articular surface of the second vertebra is the facet joint (1d) between the two vertebrae. The second screw (30b) is inserted through the posterior cortex of a lateral mass of the inferior-most vertebra (B).

Alternatively, the longitudinal spinal stabilizing member (20) may comprise a greater number of downwardly- and upwardly-angled bores than are actually needed to stabilize the desired number of vertebrae. By providing a larger number of bores from which to choose, this latter embodiment allows for greater flexibility in attaching the member (20) to the vertebrae in order to accommodate variations in patient size. Consequently, the first and second screws will only be inserted into those bores which are aligned over the desired locations of penetration of the vertebrae to be stabilized.

The present invention thus allows for a total of three cortices of each vertebra (i.e. 1a, 1b, and 1c) to be engaged by each screw, provided more than two vertebrae are to be stabilized. However, only two cortices (1a and 1b) are engaged in the superior-most vertebra (A), and only two cortices (1a and 1c) are engaged in the inferior-most vertebra (B). A minimum of at least two adjacent vertebrae must be fixed in this embodiment. Thus, if only two adjacent vertebrae are stabilized, the inferior-most vertebra would also serve as the second vertebra subjacent to the first vertebra. The preferred depth ($D_1$) of the bores created by the screws is dependant upon the anatomy of the patient, and therefore will vary from patient to patient. However, based on an extensive quantitative anatomical study performed on ten cadavers, the preferred depths ranged from about 8 mm to about 18 mm. In practice, however, bore depths outside this range may be necessary, depending on the size of the spine as well as the nature and extent of the injury, and therefore each patient must be evaluated individually.

As already discussed, only a total of two cortices are engaged in the inferior-most vertebra due to the insertion of an upwardly-angled screw (30b) into the posterior cortex of a lateral mass of the vertebra (1a). The reason for not employing bicortical, downwardly-angled fixation in the inferior-most vertebra is that such a scheme would cause a violation of the subjacent facet joint (1d). That is, the second screw would ultimately penetrate the superior articular surface of another vertebra that is not meant to be stabilized. Consequently, the second screw (30b) should be manufactured of sufficient length so as to not violate the anterior cortex of the lateral mass to ensure that the vertebral artery and cervical nerve root are not injured. As with the depth ($D_1$) of the downwardly-angled bores, the depth ($D_2$) of the bore created by the second screw will vary from patient to patient depending upon the size of the spine and the nature and extent of injury, for example.

The combination of downwardly- and upwardly- angled screw placements employed in the present invention allows for tri-cortical and bi-cortical bony purchase through the spine, preferably the cervical spine, without significant threat to the vertebral artery or cervical nerve root. Based on the same anatomical study discussed above, a preferred range of upward angles ($\beta$) is from about 20 to about 60 degrees, more preferably from about 40 to about 50 degrees, and most preferably about 45 degrees. Similarly, the preferred range of downward angles ($\alpha$) is from about 20 to about 60 degrees, more preferably from about 40 to about 50 degrees, and most preferably about 45 degrees. In addition, the most preferred length for the first screws based on this study is from about 10 mm to about 12 mm, and for the second screws (i.e. upwardly-angled screws), the preferred length is from about 5 mm to about 10 mm. These preferred angles and areas of placement on the posterior cortex of the lateral mass of the vertebrae were determined based upon the quantitative anatomic study of the lateral masses of the bones of the cervical spine discussed above. Table 1 is a tabulation of the measured lateral mass inferior angles and the AP (i.e. anterior/posterior) dimension of the vertebrae at each level.

Moreover, the use of a locking screw in the present invention is most preferred for maximum stability and minimal risk of screw pull-out. However, non-locking screws and other types of fasteners, including, but limited to, bolts, pins, and nails, may also be used. A preferred locking screw from a safety standpoint is a novel locking screw, as described herein. As discussed later, if the present inventive locking screw is employed, the lips (25a and 25b) of the longitudinal spinal stabilizing member (20) can also be crimped inward to lock the screw into the member (20). Other locking screws can also be used in the present invention. For example, the locking screw used in the cervical spinal locking plate manufactured by AO/Synthes ("CSLP") discussed herein could be used with the present invention without any modification to the inventive longitudinal spinal stabilizing device. With a slight modification to the invention, namely the addition of threads to the angled bores of the inventive longitudinal spinal stabilizing member, the "double-threaded" locking screw manufactured by the AMS Company could also be employed. It is further contemplated that one of ordinary skill in the art who first has the benefit of this invention's teachings and suggestions could make the necessary modifications to the inventive longitudinal spinal stabilizing device to accommodate Danek's ORION locking screw system.

While the inventive posterior longitudinal stabilizing member may be of any desired length and thickness, it preferably should be as thin as possible to minimize contact with nerves and blood vessels underlying the skin covering the vertebrae. A preferred thickness (T) of the plate is from about 2.0 mm to about 4.0 mm, more preferably from about 1.5 mm to about 3.0 mm.

Figure 1:
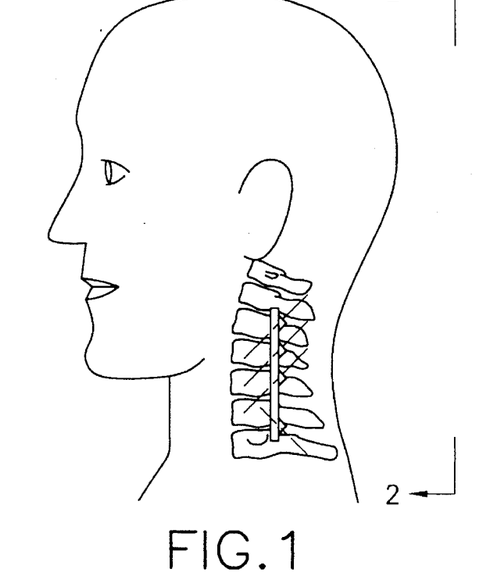
FIG. 1 is a side view of the head and neck showing attachment of the present inventive posterior longitudinal stabilizing device to the cervical vertebrae.
Figure 2:
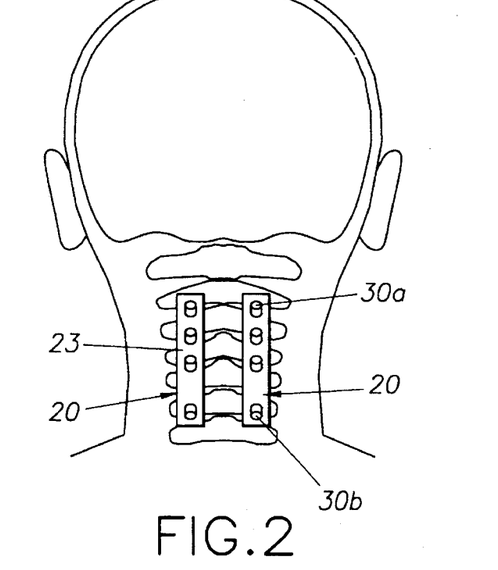
FIG. 2 is a posterior view of the neck region taken along lines 2—2 of FIG. 1 showing bilateral attachment of two posterior longitudinal stabilizing devices of the present invention.

FIG. 2 illustrates the most preferred embodiment of the present inventive method, namely the attachment of two longitudinal spinal stabilizing members (20) positioned bilaterally to one another along the posterior surfaces of the vertebrae, preferably the cervical vertebrae C-2 through C-7. Alternatively, two longitudinal spinal stabilizing members can be attached to the posterior surfaces of at least two adjacent thoracic vertebrae for optimal stabilization.

TABLE 1

Quantitative anatomy of the posterior cervical spine (taken from 10 human cadavers)

| Vertebral Level | Inferior Facet Angle | Degrees | AP Lateral Mass Dimensions |
|---|---|---|---|
| C-3 | 47.6 | (4.0) | 9.5 (1.5)* |
| C-4 | 39.8 | (5.2) | 9.9 (2.5)* |
| C-5 | 34.4 | (2.9) | 9.0 (1.3)* |
| C-6 | 24.7 | (1.3) | 8.9 (2.0)* |
| C-7 | 20.2 | (2.5) | 7.3 (1.3)* |
| Overall Mean | 33.4 | (10.5) | 8.9 (1.9)* |

*Mean (Standard Deviation)

Figure 16:
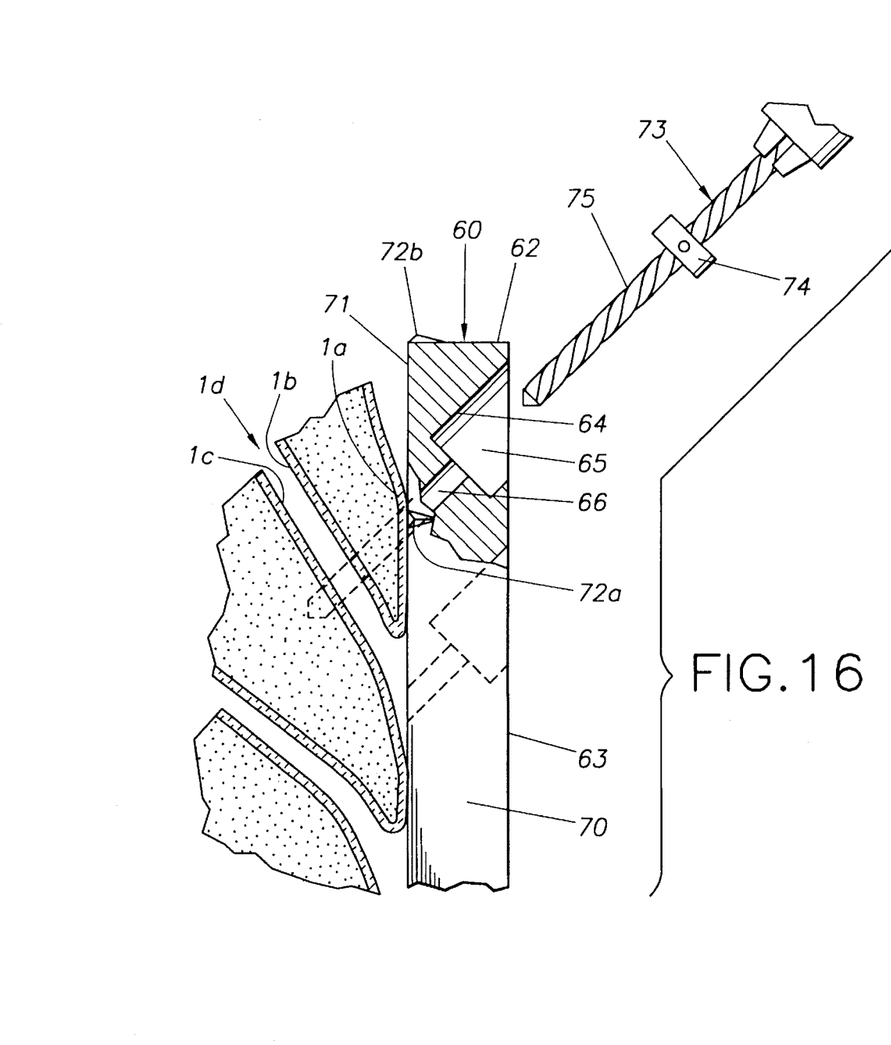
FIG. 16 is a cross-sectional side view of the vertebrae and of the inventive drill guide aligned along the posterior surface of the vertebrae.

In an alternate embodiment of the present inventive method, posterior spinal stabilization may be achieved by eliminating the inventive longitudinal spinal stabilizing member (20). In this embodiment, as shown in FIG. 16, each of at least one, and preferably two, first bores are drilled at a downward angle, first through the posterior cortex of the lateral mass (1a), and then through the inferior articular surface of the first vertebra (1b). Next, at least one, and preferably two, second bores are drilled at a downward angle, each through the superior articular surface of the second vertebra subjacent (1c) to the first vertebra. Similarly, at least one, and preferably two, third bores are drilled at an upward angle, each through the posterior cortex of the lateral mass of the inferior-most vertebra (1a), as most clearly shown in FIG. 3. The preferred depths of the bores are dependant upon the size of the spine and the nature and extent of the injury, and thus will vary from patient to patient. However, based upon the same anatomical study discussed herein for the inventive method for posterior spinal stabilization illustrated in FIGS. 3–6, the preferred combined depths for the first and second bores range from about 8 mm to about 18 mm, and the preferred depth for the third bore range from about 5 mm to about 10 mm.

Figure 17:
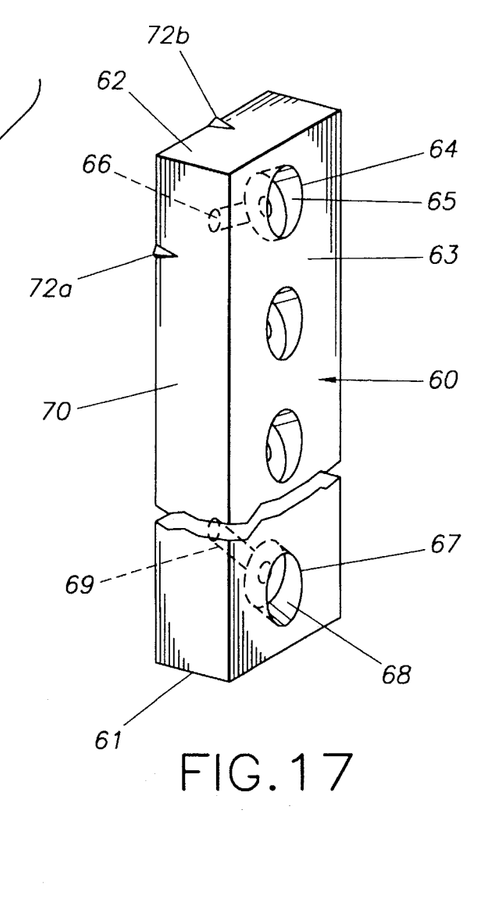
FIG. 17 is a perspective view of the inventive drill guide for drilling holes into the vertebrae according to the present inventive method.

To obtain the optimal bore angle and depth according to the present invention, a jig or drill guide (60), as shown in FIGS. 16 and 17, may be used. The inventive drill guide (60) has a superior wall (62), an inferior wall (61), a posterior wall (63), an anterior wall (71) and two side walls (70). Designed very similarly to the present inventive longitudinal spinal stabilizing member (20), the inventive drill guide (60) further comprises at least one bore (64) positioned at a downward angle through the posterior (63) and anterior (71) walls. Each bore (64) comprises an upper section (65) wide enough to accommodate a drill stop (74) and a lower section (66) that is of a sufficient diameter to allow insertion of the drill bit (75). The inventive drill guide (60) may be aligned along the posterior surfaces of the lateral masses of the desired vertebrae. Accurate vertical positioning of the drill guide may be better attained by utilizing a pointer (72a), which is located on a side wall (70) of the drill guide and which may be moved to the desired point of penetration of the drill bit (75) into the posterior cortex of the lateral mass of the vertebra (1a). Another pointer (72b) located on the superior wall (62) of the drill guide may also be used to aid in proper horizontal alignment of the drill guide along the vertebrae. Once the drill guide is in the correct position, bores may be drilled into the vertebrae using a drill (73). Preferably, the drill (73) comprises a drill stop (74) which may be adjusted along the drill bit (75) to obtain the desired bore depth.

Figure 14:
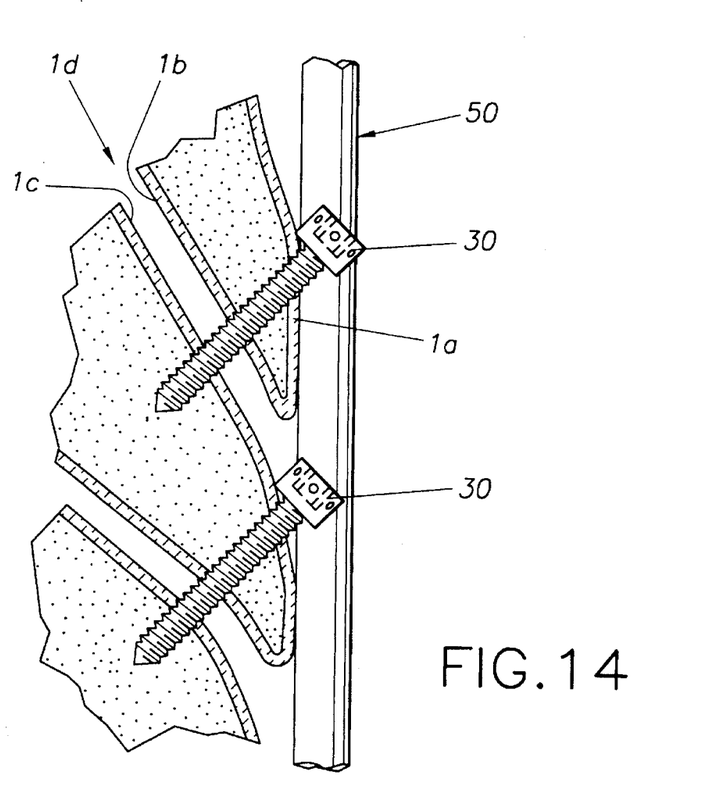
FIG. 14 is a cross-sectional side view of an alternate inventive method of posterior spinal fixation using screws and a spinal fixation rod.

Alternatively, a longitudinal rod or plate (50), may be placed along the posterior surface of the vertebrae and between the bores, as shown in FIG. 14. Once the rod (50) is in place, the screws are inserted into the downwardly- and upwardly-angled bores, as already described for the preferred embodiment of the invention. A separate device may be used to attach the screws to the spinal rod or plate (50), and consequently stabilize the vertebrae. Suitable devices for attaching the screws to the spinal rod or plate include, but are not limited to, a clamp and connecting rod assembly and a locking bolt.

While the present inventive longitudinal spinal stabilizing device is the most preferred, other longitudinal spinal stabilizing devices may also be used in practicing the inventive method for posterior spinal stabilization if desired. That is, the use of other spinal stabilizing devices are within the scope of the present invention, provided the screws are positioned in the vertebrae as described herein, namely in terms of the angle and location of penetration (i.e. penetration of the posterior cortex of the lateral masses and penetration of the superior and inferior articular surfaces of a first vertebra and a second subjacent vertebra, respectively).

The inventive posterior longitudinal spinal stabilizing member may be formed of materials typically employed by those of ordinary skill in the art in the manufacture of other orthopedic implants, including other internal spinal implants and devices. Examples of suitable materials include, but are not limited to, stainless steel, titanium, and vanadium, for example. Preferably, titanium or a titanium alloy may be used.

Locking Screw System:

The present invention is also directed to a novel locking screw and locking device which may be used in orthopedic devices. Examples of suitable orthopedic devices include the present inventive posterior spinal stabilizing device as well as other devices used for anterior or posterior spinal fixation and for which a locking screw is desired. Furthermore, the present inventive locking screw may be used in the present inventive posterior occipital/spinal fixation device later described and claimed herein. For ease of explanation, the present inventive locking screw will be described with reference to the present inventive posterior longitudinal spinal stabilizing devices and method. However, it is recognized that the inventive locking screw may be used in essentially any orthopedic device and bony region in which a locking screw is typically employed.

Figures 10, 11, 12:
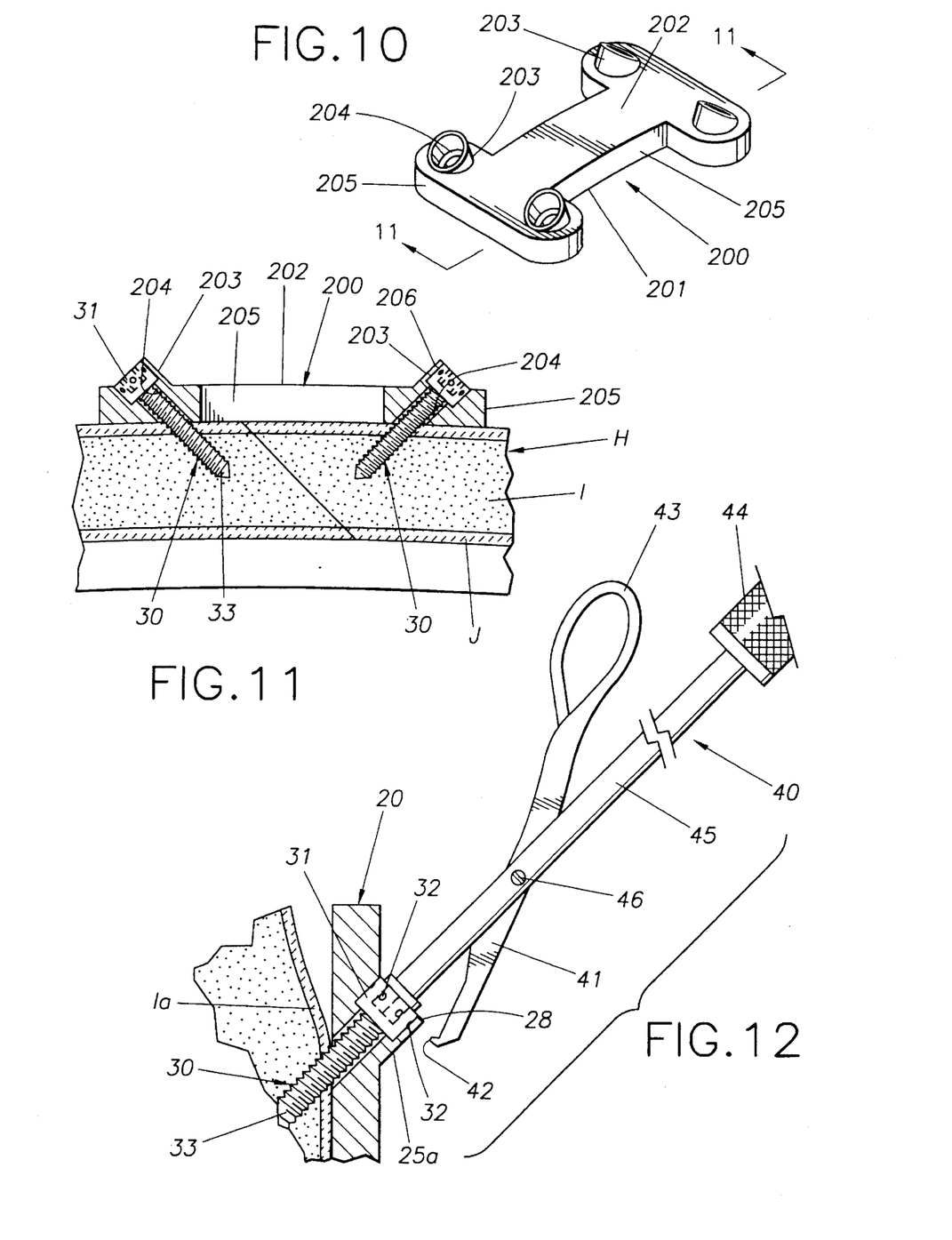
FIG. 10 is a perspective view of the alternate embodiment of the inventive plate useful in unicortical skull fragment stabilization.
FIG. 11 is a cross-sectional side view of both embodiments of the present inventive plate taken along line 11—11 of FIG. 10, showing angled unicortical engagement of the occiput using the inventive locking screw.
FIG. 12 is a cross-sectional side view of the inventive posterior spinal stabilizing device containing the preferred embodiment of the inventive locking screw and crimping tool for crimping the lip of the device into the head of the screw.
Figure 13:
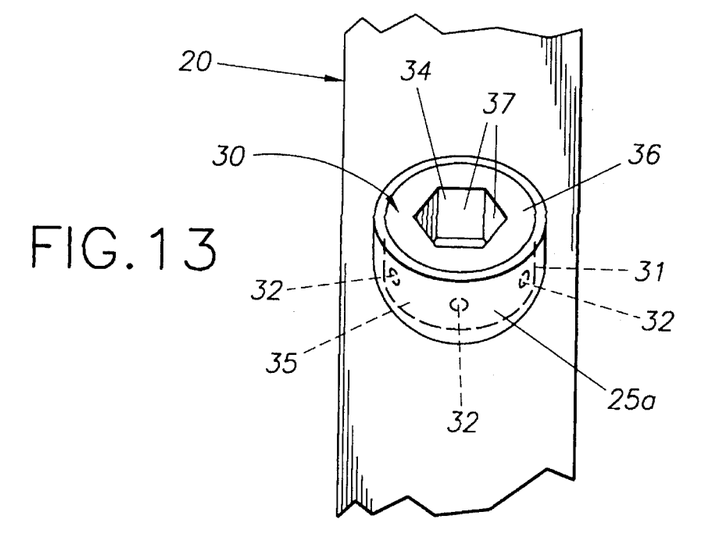
FIG. 13 is a posterior or front view of the inventive locking screw engaged within the spinal stabilizing device illustrated in FIG. 12.

Referring now to FIGS. 12–13, the inventive locking screw (30) comprises a head (31), preferably a head that is cylindrical in shape, and a threaded longitudinal cylindrical piercing member (33) integral with the head. The head (31) further includes an exterior surface (35), which defines the circumference of the head, and at least one depression (32) or locking means positioned on the exterior surface of the head for locking the head within the device via crimping engagement of the lip (25a,b), for example, into the depression. The lip (25a,b) extends from and is integral with the posterior surface of the longitudinal spinal stabilizing member (20) and is positioned about the bore in which the inventive screw (30) is to be inserted. The head (31) of the inventive screw further comprises a top portion (36) integral with the exterior surface of the head (35), and a socket (34) for insertion of a tool for engaging the locking screw through the longitudinal spinal fixation member (20) and into the vertebrae. Preferably, the socket (34) has from about three to about eight sides (37), more preferably six sides.

Once the inventive screw is placed into the bore of the longitudinal spinal stabilizing member (20) and then properly engaged within the vertebra or vertebrae, a crimping tool is used to crimp the lip (25a,b) into the depression (32) or locking means and thereby locks the screw into the member. An example of a suitable crimping tool (40) is that shown in FIG. 12. The inventive tool comprises an elongated rod (45) having a preferably knurled knob (44) at one end for gripping the rod. Secured to the elongated rod is an arm (41) having at one end a handle (43) and at the other end a crimping means (42) for crimping a portion of the lip (25a,b) into the screw. A fastener (46), such as bolt or screw, is used to secure the arm (41) to the elongated rod (45), allowing pivotal movement of the arm about the rod.

As shown in FIG. 12, the crimping means may be in the form of a small tooth (42) extending from the elongated rod (45) at an angle towards the screw. The tooth (42) functions to crimp or deform the metal of the orthopedic device into a locking means (32) of the locking screw head. In one embodiment of the inventive tool, the elongated rod (45) is inserted into the socket (34) of the screw, afterwhich torque is applied to the knob (44) to drive the screw into the vertebra. Alternatively, another tool may be used to drive the screw into the vertebra, while the inventive crimping tool is used only to lock the screw into the orthopedic device by crimping, as described above.

Once the inventive screw is in place, the lip (25a,b) may be crimped into one or more of the depressions or locking means (32), as shown in FIG. 12, by squeezing the handle (43) and knob (44) of the tool together to cause the tooth (42) to crimp or deform a portion of the lip (25a,b) into the depression or locking means. The screw may be later removed by breaking away the crimp, i.e. the top portion (28) of the lip which is not engaged into the depression (32).

In the preferred embodiment, the head of the screw (31) is cylindrically-shaped; however, the head may have a plurality of sides, preferably from about three to about eight sides (not shown), and more preferably six sides. As shown in FIGS. 12 and 13, the exterior surface of the head preferably includes from about one to about twelve depressions, more preferably from about six to about eight depressions. In the most preferred embodiment, each depression (32) is aligned with each side (37) of the socket (34), as shown in FIG. 13, to ensure that the tooth (42) of the crimping tool (40) will crimp the orthopedic device, such as the lip (25a,b) in the present invention, into a depression (32) or locking means, thereby locking the screw within the device. The engaging means of the crimping tool, which fits into the screw head, and the crimping tooth, are both at the same distance from the tool pivot (i.e. the location of the fastener (46)). The socket (34) is made to have a depth such that, when the tool is inserted into it, the tooth always meets a depression.

The inventive locking screw may also be used to engage other orthopedic devices as well as bones and bony regions other than the vertebrae and skull. Whether the inventive screw is engaged into an orthopedic device and/or into a bone, the novel feature of the inventive screw is primarily its locking mechanism, namely the crimping of a portion of an orthopedic device into one or more of the depressions (i.e. locking means) present on the screw head.

The present inventive locking screw may be formed of any material typically used in the manufacture of orthopedic locking screws. A preferred metal is pure titanium or stainless steel.

Figure 8:
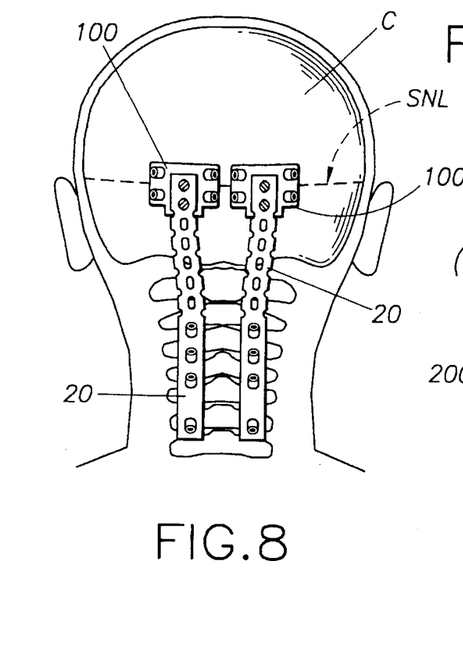
FIG. 8 is a posterior or front view illustrating the attachment of two of the inventive longitudinal spinal stabilizing devices to the posterior surface of cervical vertebrae and to two of the inventive plates positioned bilaterally to one another along the superior nuchal line (SNL) of the occiput.

Occipital/Spinal Fixation:

The present invention is also related to a modular method and device for posterior occipital/spinal fixation. Referring now to FIGS. 7 and 8, the present invention is directed to a novel fixation device comprising a plate (100) which may be attached to an optimal position on the occiput, preferably the thickest part of the occiput, to avoid penetration of the intracranial venous sinuses and the brain. In the present invention, the optimal position for attachment of the inventive plate (100) is along the superior nuchal line (SNL).

The modular design of the present invention allows for independent placement of the plate or plates and the longitudinal spinal stabilizing device or devices, for example. This is particularly desirable when precision is absolutely necessary for safe insertion of cervical spine lateral mass screws, for example, which would effectively dictate the position and orientation of a combination occipital/cervical plate beyond any substantial control of the surgeon. The foregoing situation is improved by employing bendable occipital/cervical plates, such as the laterally bendable reconstruction plates manufactured by Synthes, for example; however, the surgeon still has little choice in the exact positioning of the cranial fixation screws. Separate attachment of a plate to the skull and a spinal fixation device to the spine eliminates all of these problems and allows for safer stabilization.

In addition to the use of a modular system for occipital/spinal fixation, the present invention is related to a novel fixation device for occipital/spinal fixation which allows for unicortical purchase of the skull. Referring now to FIG. 7, the present invention comprises the use of a plate (100) having a posterior surface (102) and an anterior surface (101), and which further comprises at least two, and preferably four, angled first bores (104) positioned bilaterally to one another through the plate at an angle. Preferably, a lip (103), similar to the lips (25a,b) present on the inventive posterior longitudinal spinal stabilizing member (20), is positioned about each bore and extends from the posterior surface (102) of the plate (100), and functions in part to maintain the angle of the bore (i.e. the lip's angle of extension is the same as the angle of the bore). The lip also aids in the locking mechanism of a locking screw.

FIG. 10 is an alternate embodiment (200) of the present inventive plate useful for stabilizing a skull fracture, for example. It is important to note that while FIG. 11 is a cross-sectional view of the plate (200) depicted in FIG. 10, the angle of the bores and the position of the screws shown in FIG. 11 are identical to that of the embodiments of the plate designed for attachment to a posterior spinal stabilizing device. Thus, all references to FIG. 11 apply equally to the embodiments depicted in FIGS. 7, 15, and 15a.

Referring now to FIGS. 7 and 11, the present inventive plate further includes a means for connecting the plate to the occiput (C). In the preferred embodiment, the connecting means is a first screw (30) which is inserted into each of the first bores (104 and 204). Based upon the same anatomical study discussed above, a preferred length of each screw (30) is from about 3 mm to about 16 mm, more preferably about 6 mm, to allow only for penetration of the posterior cortex of the occiput (H), as opposed to engagement of both the posterior (H) and anterior (J) cortices. The screw lengths actually employed, however, may vary outside this range depending upon the anatomy of the particular patient. Such unicortical engagement is not only much safer in that it eliminates the risk of penetrating the intracranial venous sinuses, but it is also just as stable as bicortical fixation by virtue of the angled engagement of the first screws (30) in the bone of the occiput. Such angled engagement of the screws, either converging towards one another (as shown in FIG. 11, for example) or diverging away from one another, further minimizes screw pull-out.

The types of screws that can be used in the present invention are preferably locking screws, including the present inventive locking screw described and claimed herein; however, as in the present inventive posterior spinal fixation device, non-locking screws may be used. If the inventive locking screw is employed, the lip (103 and 203) of the plate can also be crimped inward to lock the screw into the plate. Referring to FIG. 11, the screw may be later removed by breaking away the top portion of the lip (206) which is not crimped or engaged into the depression or locking means of the screw head.

The inventive plate is preferably formed of a relatively malleable material, such as surgical steel, titanium, and other metals and metal alloys, for example. Other materials typically used by those of skill in the art for use in orthopedic implants may also be employed. It is important that the plate be slightly concave in shape or be malleable enough so that it may be bent into a concave shape to better fit the convex contour of the occiput or other desired region of the skull.

The inventive fixation device further comprises a means for mounting the plate to a longitudinal spinal stabilizing device. In the preferred embodiment, as shown in FIG. 7, the mounting means is a slightly elevated platform (108) integral with the posterior surface of the plate (102). The platform (108) preferably includes at least one, more preferably two, second bores (106) for engagement with a longitudinal spinal stabilizing device by a second connecting means, such as a screw (109). In the most preferred embodiment, the platform has at least two sets of at least one, more preferably two, bores (106) to allow for greater flexibility for attachment of the longitudinal spinal device to the plate (100). Alternatively, the platform (108) may include at least two second bores (107) positioned bilaterally to one another in a horizontal plane through which a second connecting means, preferably at least one wire, may be threaded to secure a longitudinal spinal stabilizing device, such as a rod, for example, to the platform (108).

Alternatively, the platform may be eliminated, and instead the longitudinal spinal stabilizing device is mounted directly to the plate by a second connecting means, such as a screw or wire. Thus, in this embodiment, the mounting means is simply at least one second bore (106) positioned centrally through the posterior (102) and anterior surfaces (101) of the plate.

The most preferred longitudinal spinal stabilizing device is the present inventive posterior spinal stabilizing device discussed herein. As shown in FIG. 6, the superior end (22) of the inventive longitudinal spinal stabilizing member (20) includes at least one, and preferably two, bores (26c) aligned vertically. These bores, preferably threaded, are in a "neutral" (i.e. horizontal) position, as opposed to being angled, to receive a screw or wire for connecting the member (20) to the mounting means, such as a platform (108), for example.

Alternatively, the superior end (22) of a longitudinal spinal stabilizing device, including the present invention, may be attached directly to the occiput; however, this is not a preferred method.

The present inventive spinal stabilizing member (20) preferably contains scallops (27) along the outer edges of the member to afford some flexibility to the member as well to serve as points at which the member can more easily be broken or cut away for purposes of customizing the member to a desired size. This latter aspect of the invention (i.e. the ability to shorten the inventive longitudinal spinal stabilizing member) is particularly useful in that it avoids the necessity of an excessive number of different sized members during surgery. Thus, a more preferred embodiment of the inventive longitudinal spinal stabilizing member (20) would contain several such neutral bores (26c) to allow for a greater number of choices of member size.

FIG. 8 illustrates the most preferred embodiment of the present invention, wherein two longitudinal spinal stabilizing devices, preferably the present inventive longitudinal spinal stabilizing device, are employed. In this embodiment, the two longitudinal spinal stabilizing members (20) are positioned bilaterally to one another along the posterior surfaces of the vertebrae, and the superior ends (22) of each member are attached to a separate plate (100) connected to the occiput (C).

Figure 15:
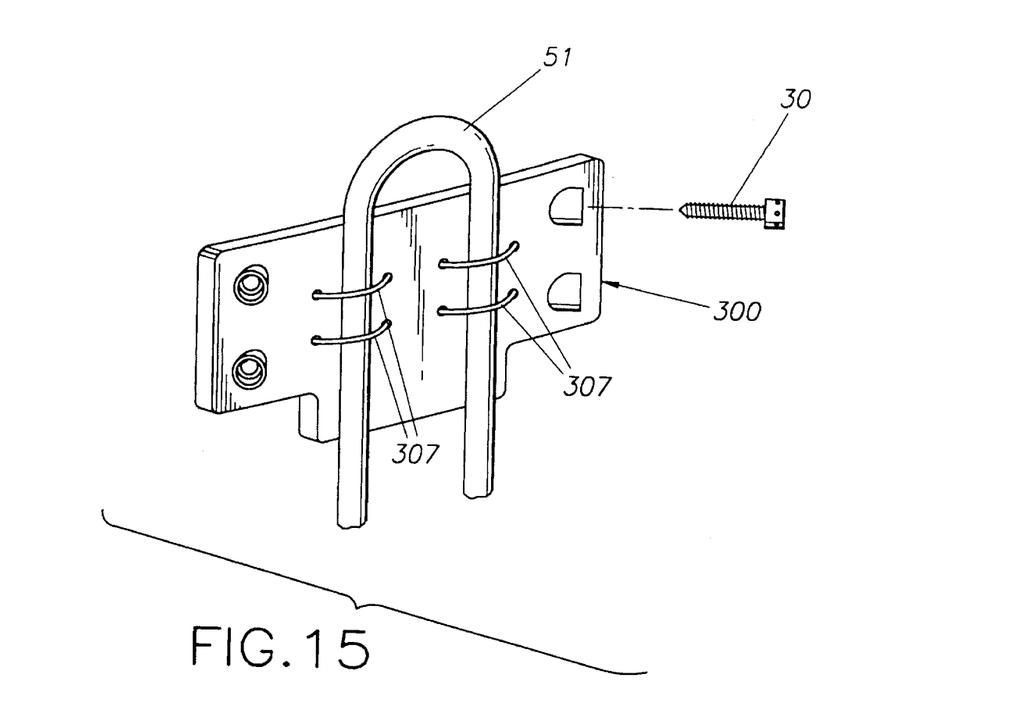
FIG. 15 is a perspective view of a third embodiment of the inventive method of occipital/spinal fixation illustrating attachment of a single rod to a single plate.
Figure 15A:
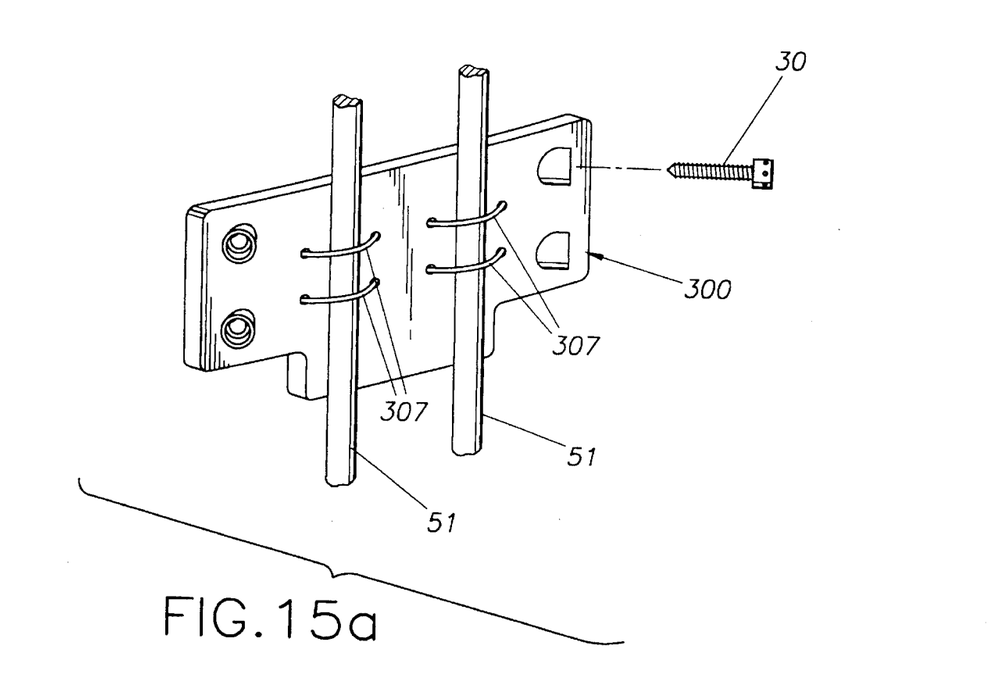
FIG. 15a is a perspective view of a third embodiment of the inventive method of occipital/spinal fixation illustrating attachment of two separate rods to a single occipital plate.

Alternatively, a single spinal rod (51), for example, may be bent, as illustrated in FIG. 15, and mounted to a single plate (300) by wires (307), for example. Similarly, two separate rods could be attached to a single plate (300) as shown in FIG. 15a. Or in lieu of two rods, two other types of longitudinal spinal stabilizing devices, including the present inventive longitudinal stabilizing member (20), may be mounted to a single plate (300) by an appropriate connecting means. Suitable connecting means include, but are not limited to, screws, wires, bolts, pins, and other similar types of fasteners. While these latter embodiments of the present invention as shown in FIGS. 15 and 15a are not the most preferred methods of occipital/spinal stabilization, they may in rare cases be necessary when it is impossible or extremely difficult to attach two plates to the occiput.

Unicortical skull and general bone stabilization:

The present invention is also directed, in certain embodiments, to a method of unicortical stabilization of skull bone due to a fracture or a craniotomy and employs a minor variation of the inventive occipital fixation device, namely the plate. Referring to FIG. 10, the inventive plate (200) may be shaped like a "dogbone" and does not require a platform or any other means for mounting the plate to another device. The term "craniotomy" as used herein refers to the surgical removal of a portion of the skull, as in a partial craniectomy. As for the embodiment of the plate illustrated in FIGS. 7, 15, and 15a, for example, the plate (200) depicted in FIGS. 9, 9a, 9b, and 10 also has a posterior surface (202) and an anterior surface (201), as well as at least two, and preferably four, angled first bores (204) positioned bilaterally to one another through the plate at an angle, as shown in FIGS. 10 and 11.

Figure 9:
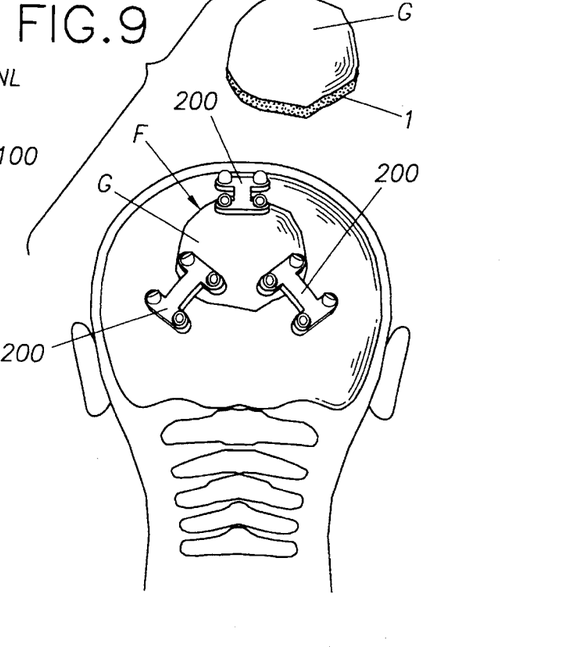
FIG. 9 is a perspective view of the skull and a skull fragment and illustrates the present inventive method of unicortical skull fragment or fracture stabilization using an alternate embodiment of the inventive plate.

As shown in FIG. 9, for stabilization of a skull fragment in the repair of a craniotomy, the skull fragment (G) is inserted into a skull opening formed from the craniotomy. The skull opening and the outer edge (1) of the skull fragment (G) define a junction (F). The present inventive method comprises aligning the plate (200) over the junction (F) on the posterior surfaces of the skull and skull fragment such that the junction (F) is located between the bores (204).

As shown in FIG. 11, preferably a screw (30), more preferably the inventive locking screw, is inserted into each of the bores to penetrate the posterior cortex of the skull (H) for unicortical engagement. Other fasteners may be employed in lieu of screws, including, but not limited to, bolts, pins, nails, and the like. As for the present inventive method for occipital/spinal fixation, the screws are positioned bilaterally to one another at either a converging angle (as shown in FIG. 11) or at a diverging angle. The skull fragment is thus stabilized to prevent it from subsiding into the brain and to promote a more cosmetically pleasing repair. Once the skull has healed, the plate may be removed.

Similarly, the present inventive plate may be used to stabilize a skull fracture, the only difference being that the junction (F), as shown in FIG. 9, is now the line of fracture. In this use of the inventive plate, the fracture is stabilized to prevent further damage to the skull as well as to promote bone growth at the line of fracture (F) for better healing.

Figure 9A:
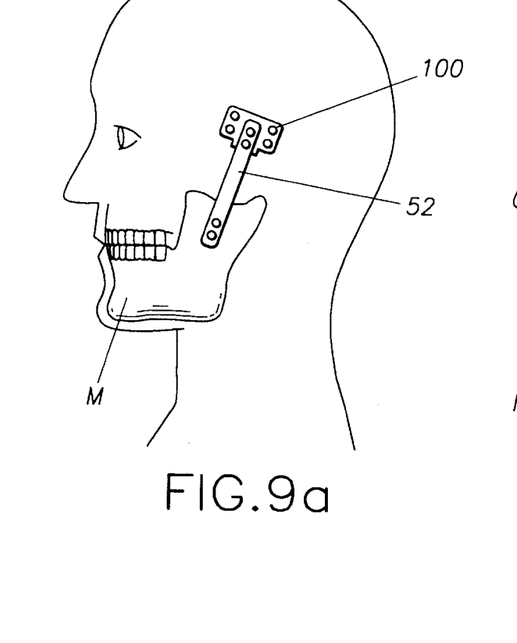
FIG. 9a is a side view of the skull illustrating fixation of the mandible to the skull using one inventive plate and a longitudinal fixation device.
Figure 9B:
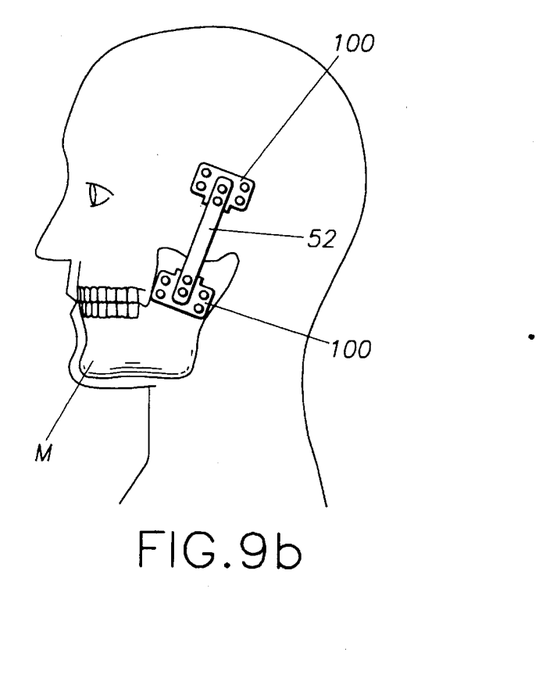
FIG. 9b is a side view of the skull illustrating fixation of the mandible to the skull using two inventive plates and a longitudinal fixation device.

The inventive plate used for unicortical skull stabilization and posterior occipital/spinal stabilization may also be used for general bone stabilization in other regions of the skull and body. FIGS. 9a and 9b illustrate one embodiment of the inventive method for stabilizing a mandible (M) of a skull. Preferably, at least one inventive plate (100) is connected to a posterior surface of the skull. One end of at least one longitudinal orthopedic stabilizing device (52) is then attached directly to the mandible (M), while the other end of the device (52) is attached to the plate (100). Alternatively, a second plate (100) can also be connected to the mandible (M) such that the longitudinal orthopedic device (52) is mounted to two plates, as shown in FIG. 9b.

It is also within the scope of the present invention that the inventive plates (100, 200, 300) may be used to stabilize bone and bone fractures located in regions of the body other than the skull and spine. Examples of such uses include, but are not limited to, (1) fixation of the bones of the pelvis to the lumbar spine or to the femur, (2) fixation of the tibia to the femur or to the bones of the foot, (3) fixation of the radius or ulna to the humerus or to the bones of the hand, and (4) fixation of the scapula to the clavicle or humerus. In addition, the inventive plate may be used to stabilize fractures in a single bone located in another region of the body, including, but limited to, the bones listed above.

The foregoing disclosure and description of the invention are illustrative and explanatory thereof, and changes in the size, shape, and materials, as well as in the details of the illustrated construction may be made without departing from the spirit of the invention.

What is claimed is:

1. A method for internal posterior spinal stabilization, comprising (a) drilling each of at least one first bore at a downward angle through a posterior cortex of a lateral mass of a first vertebra of a spine and an inferior articular surface of said first vertebra of a spine; (b) drilling each of at least one second bore at a downward angle through a superior articular surface of a second vertebra subjacent to said first vertebra; (c) drilling each of at least one third bore at an upward angle through a posterior cortex of a lateral mass of an inferior-most vertebra; and (d) inserting a first screw through said each of at least one first bore and said second bore to stabilize said first and second vertebrae of a spine.

2. The method of claim 1, wherein said steps of drilling comprise drilling each of said at least one first, second, and third bores at from about 35 to about 60 degree angles.

3. The method of claim 1 wherein said first and second vertebrae are cervical spinal vertebrae in a series of at least two adjacent vertebrae selected from the group consisting of vertebrae C-2, C-3, C-4, C-5, C-6, and C-7 of said spine.

4. The method of claim 3, wherein said steps of drilling comprise drilling each of said at least one first, second, and third bores at from about 35 to about 60 degree angles.

5. A posterior spinal stabilizing device for a spine, comprising:
   (A) a longitudinal spinal stabilizing member comprising (a) a superior end, (b) an inferior end, (c) an anterior surface, (d) a posterior surface, (e) at least one first bore contained therethrough and positioned at a downward angle of from about 20 degrees to about 60 degree, and (f) at least one second bore contained therethrough and positioned at an upward angle of from about 20 degrees to about 60 degrees, wherein said at least one second bore is located on the inferior end of said member;
   (B) a first screw for engagement within each of at least one said first bore to engage two vertebrae of said spine, one of which is an inferior-most vertebra of the two; and
   (C) a second screw for engagement within each of at least one said second bore to engage the inferior-most vertebra.

6. The device of claim 5, wherein said upward angle is from about 40 degrees to about 50 degrees and said downward angle is from about 40 degrees to about 50 degrees.

7. The device of claim 6, wherein said upward angle is about 45 degrees and said downward angle is about 45 degrees.

8. A posterior spinal stabilizing device for a spine, comprising:
   (A) a longitudinal spinal stabilizing member comprising (a) a superior end, (b) an inferior end, (c) an anterior surface, (d) a posterior surface, (e) at least one first bore contained therethrough and positioned at a downward angle, and (f) at least one second bore contained therethrough and positioned at an upward angle, wherein said at least one second bore is located on the inferior end of said member;
   (B) a first screw for engagement within each of at least one said first bore to engage two vertebrae of said spine, one of which is an inferior-most vertebra of the two;
   (C) a second screw for engagement within each of at least one said second bore to engage the inferior-most vertebra; and
   (D) a raised lip integral with and extending from said posterior surface and positioned about said first and second bores, and wherein each said first screw and said second screw is a locking screw comprising a head and a threaded longitudinal cylindrical piercing member integral with said head, said head comprising (a) an exterior surface defining the circumference of said head, (b) at least one depression positioned on said exterior surface for crimping engagement within said raised lip, and (c) a top portion integral with said exterior surface, wherein said top portion has a socket for insertion of a crimping tool for engaging said socket of said screw.

9. A method for internal posterior spinal stabilization of a spine, comprising mounting a longitudinal spinal stabilizing member, with at least two screws, to at least two vertebrae of said spine, said vertebrae including an inferior-most vertebra, by (a) inserting a first screw through each of one or more at least one downwardly-angled bore contained through said longitudinal spinal stabilizing member, and then penetrating with said first screw a posterior cortex of a lateral mass of a first vertebra, an inferior articular surface of said first vertebra, and a superior articular surface of a second vertebra subjacent to said first vertebra; and (b) inserting a second screw through each of one or more at least one upwardly-angled bore contained through the inferior end of said longitudinal spinal stabilizing member, and then penetrating a posterior cortex of a lateral mass of said inferior-most vertebra.

10. The method of claim 9, wherein said vertebrae are cervical vertebrae in a series of at least two adjacent vertebrae selected from the group consisting of vertebrae C-2, C-3, C-4, C-5, C-6, and C-7 of said spine.

11. The method of claim 9, wherein said vertebrae are thoracic vertebrae of said spine.

12. A method for internal posterior spinal stabilization of a spine, comprising:
   (a) drilling each of at least one first bore at a downward angle through a posterior cortex of a lateral mass of a first vertebra of a spine and an inferior articular surface of said first vertebra of a spine;
   (b) drilling each of at least one second bore at a downward angle through a superior articular surface of a second vertebra subjacent to said first vertebra;
   (c) drilling each of at least one third bore at an upward angle through a posterior cortex of a lateral mass of an inferior-most vertebra;
   (d) aligning a longitudinal spinal stabilizing device comprising downwardly-angled bores and upwardly-angled bores along said vertebrae;
   (e) inserting a first screw through each of said downwardly angled bores of said device and said each of at least one first bore and said second bore, respectively, to stabilize said first and second vertebrae of said spine; and
   (f) inserting a second screw through one of said upwardly angled bores of said device and said at least one third bore of said inferior-most vertebra, respectively.

13. The method of claim 12, wherein said steps of drilling comprise drilling each of said at least one first, second, and third bores at from about 35 to about 60 degree angles.

14. The method of claim 12, wherein said first and second vertebrae are cervical spinal vertebrae in a series of at least two adjacent vertebrae selected from the group consisting of vertebrae C-2, C-3, C-4, C-5, C-6, and C-7 of said spine.

15. The method of claim 14, wherein said steps of drilling comprise drilling each of said at least one first, second, and third bores at from about 35 to about 60 degree angles.

16. A method for internal posterior spinal stabilization of a spine, comprising:
   (a) drilling each of at least one first bore at a downward angle through a posterior cortex of a lateral mass of a first vertebra of a spine and an inferior articular surface of said first vertebra of a spine;
   (b) drilling each of at least one second bore at a downward angle through a superior articular surface of a second vertebra subjacent to said first vertebra;
   (c) drilling each of at least one third bore at an upward angle through a posterior cortex of a lateral mass of an inferior-most vertebra;
   (d) inserting a first screw through each of said at least one first bore and said second bore;
   (e) inserting a second screw through each of said at least one third bore of said inferior-most vertebra; and
   (f) attaching a spinal fixation rod to said first and second screws.

17. The method of claim 16, wherein said steps of drilling comprise drilling each of said at least one first, second, and third bores at from about 35 to about 60 degree angles.

18. The method of claim 16, wherein said first and second vertebrae are cervical spinal vertebrae in a series of at least two adjacent vertebrae selected from the group consisting of vertebrae C-2, C-3, C-4, C-5, C-6, and C-7 of said spine.

19. The method of claim 18, wherein said steps of drilling comprise drilling each of said at least one first, second, and third bores at from about 35 to about 60 degree angles.

20. A posterior spinal stabilizing device for a spine, comprising:

(A) a longitudinal spinal stabilizing member comprising (a) a superior end, (b) an inferior end, (c) an anterior surface, (d) a posterior surface, (e) at least one first bore contained therethrough and positioned at a downward angle, and (f) at least one second bore contained therethrough and positioned at an upward angle, wherein said at least one second bore is located on the inferior end of said member;

(B) a first screw for engagement within each of at least one said first bore to engage two vertebrae of said spine, one of which is an inferior-most vertebra of the two; and (C) a second screw for engagement within each of at least one said second bore to engage the inferior-most vertebra;

wherein said superior end further includes at least one neutral bore contained therethrough and a mounting means for mounting said member to an occiput.

21. The device of claim 20, wherein said mounting means is a third screw engaged within each of said at least one neutral bore for mounting said superior end of said longitudinal spinal stabilizing member to said occiput.

22. The device of claim 21, wherein said mounting means further includes a plate mounted to said occiput, wherein said superior end of said longitudinal spinal stabilizing member is attached to said plate by said third screw engaged within each of said at least one neutral bore.

* * * * *